(12) United States Patent
Mou et al.

(10) Patent No.: US 11,737,676 B2
(45) Date of Patent: Aug. 29, 2023

(54) BLOOD PRESSURE MEASUREMENT MODULE

(71) Applicant: MICROJET TECHNOLOGY CO., LTD., Hsinchu (TW)

(72) Inventors: Hao-Jan Mou, Hsinchu (TW); Ching-Sung Lin, Hsinchu (TW); Wen-Yang Yang, Hsinchu (TW); Yung-Lung Han, Hsinchu (TW); Chi-Feng Huang, Hsinchu (TW); Chun-Yi Kuo, Hsinchu (TW); Yi-Ting Lu, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 359 days.

(21) Appl. No.: 17/030,436

(22) Filed: Sep. 24, 2020

(65) Prior Publication Data
US 2021/0127988 A1 May 6, 2021

(30) Foreign Application Priority Data

Oct. 31, 2019 (TW) .................................. 108139585

(51) Int. Cl.
*A61B 5/0245* (2006.01)
*A61B 5/021* (2006.01)
(Continued)

(52) U.S. Cl.
CPC ............ *A61B 5/0245* (2013.01); *A61B 5/002* (2013.01); *A61B 5/0006* (2013.01); *A61B 5/0225* (2013.01); *A61B 5/0235* (2013.01); *A61B 5/02141* (2013.01); *A61B 2562/028* (2013.01); *A61B 2562/0247* (2013.01); *A61B 2562/166* (2013.01)

(58) Field of Classification Search
CPC ..... A61B 5/0245; A61B 5/0006; A61B 5/002; A61B 5/02141; A61B 5/0225; A61B 5/0235; A61B 2562/0247; A61B 2562/028; A61B 2562/166; A61B 5/02
See application file for complete search history.

(56) References Cited

U.S. PATENT DOCUMENTS 11,454,232 B2 * 9/2022 Mou ..................... F04B 45/047
2018/0325395 A1 * 11/2018 Chen ..................... F04B 45/047
(Continued)

*Primary Examiner* — Devin B Henson
*Assistant Examiner* — Evelyn Grace Park
(74) *Attorney, Agent, or Firm* — McClure, Qualey & Rodack, LLP

(57) ABSTRACT

A blood pressure measurement module includes a top cover, a micro pump, a driving circuit board, and a pressure sensor. The top cover has a gas inlet hole, an accommodation trough, and an outlet channel. An inner wall of the accommodation trough is recessed to form a gas collection chamber in communication with the gas inlet hole, and the outlet channel is connected to a gas bag. The pressure sensor is electrically connected to the driving circuit board. The driving circuit board covers the accommodation trough of the top cover. The operation of the micro pump is controlled by the driving circuit board. The gas is continuously guided to the outlet channel and is converged at the gas bag by the micro pump. When the pressure of the gas in the gas bag measured by the pressure sensor reaches a valve value, the micro pump stops its operation.

12 Claims, 19 Drawing Sheets

(51) Int. Cl.
*A61B 5/0225* (2006.01)
*A61B 5/0235* (2006.01)
*A61B 5/00* (2006.01)

(56) References Cited

U.S. PATENT DOCUMENTS

2019/0056292 A1* 2/2019 Mou .................... F04B 45/047
2019/0133454 A1* 5/2019 Mou .................. A61B 5/02141
2019/0302075 A1* 10/2019 Mou ........................ G01N 1/22

* cited by examiner

BLOOD PRESSURE MEASUREMENT MODULE

CROSS-REFERENCE TO RELATED APPLICATION

This non-provisional application claims priority under 35 U.S.C. § 119(a) to Patent Application No. 108139585 filed in Taiwan, R.O.C. on Oct. 31, 2019, the entire contents of which are hereby incorporated by reference.

BACKGROUND

Technical Field

The present disclosure relates to a blood pressure measurement module. In particular, to a blood pressure measurement module that is ultra-thin and can be combined with a wearable electronic device or a portable device.

Related Art

In recent years, awareness of personal health care has gradually increased so that the need of regularly monitoring the self-health condition has been generated. However, since most of the instruments for examining the body health condition are fixed at their corresponding places, a person has to go to a medical service station or a hospital to obtain a health examination. Even if there are already some detection devices for household uses on the market, sizes of these devices are still too large to be carried easily. In the current efficiency-pursuing society, these detection devices are hard to meet the needs of users.

Among the various health related indexes, the most representative one should be the blood pressure. The blood vessels in one's body are like roads spreading all over the body. Thus, the blood pressure is just like the road conditions, and the condition of the blood delivery can be understood through the blood pressure. If anything happens to the body, the blood pressure will reflect it clearly.

In view of these, how to provide a device capable of accurately measuring the blood pressure of a user at any time and can be combined with a wearable electronic device or a portable electronic device such that the user can quickly check the blood pressure anytime and anywhere with the device is an issue.

SUMMARY

One object of the present disclosure is providing a blood pressure measurement module that can be combined with a wearable electronic device or a portable device, so that the user can carry the module conveniently and thus can measure the blood pressure at anytime and anywhere.

To achieve the above mentioned purpose(s), a general embodiment of the present disclosure provides a blood pressure measurement module including a top cover, a micro pump, a driving circuit board, and a pressure sensor. The top cover has a gas inlet hole, an accommodation trough, and an outlet channel. The gas inlet hole and the outlet channel are respectively disposed on different surfaces of the top cover. The gas inlet hole and the outlet channel are respectively in communication with the accommodation trough. An inner wall of the accommodation trough is recessed to form a gas collection chamber in communication with the gas inlet hole, and the outlet channel is connected to a gas bag. The micro pump is disposed in the accommodation trough to cover the gas collection chamber. The driving circuit board covers the accommodation trough, and the driving circuit board controls operation of the micro pump. The pressure sensor is fixedly disposed on the driving circuit board and electrically connected to the driving circuit board. The driving circuit board covers the accommodation trough of the top cover so as to detect a pressure of gas guided into the accommodation trough. The operation of the micro pump is controlled by the driving circuit board for a gas transmission, so that a gas outside the top cover is guided into the accommodation trough through the gas inlet hole. The gas is continuously guided to the outlet channel and is converged at the gas bag by the micro pump, whereby the gas inflates the gas bag and the gas bag presses skin of a user, so that a blood pressure of the user is measured through the pressure sensor. When the pressure of the gas in the gas bag measured by the pressure sensor reaches a valve value, the driving circuit board controls and stops the operation of the micro pump so as to complete a pressure collection process of the gas bag.

BRIEF DESCRIPTION OF THE DRAWINGS

The disclosure will become more fully understood from the detailed description given herein below for illustration only, and thus not limitative of the disclosure, wherein.

DETAILED DESCRIPTION

The present disclosure will now be described more specifically with reference to the following embodiments. It is to be noted that the following descriptions of different embodiments of this disclosure are presented herein for purpose of illustration and description only, and it is not intended to limit the scope of the present disclosure.

Figure 1A:
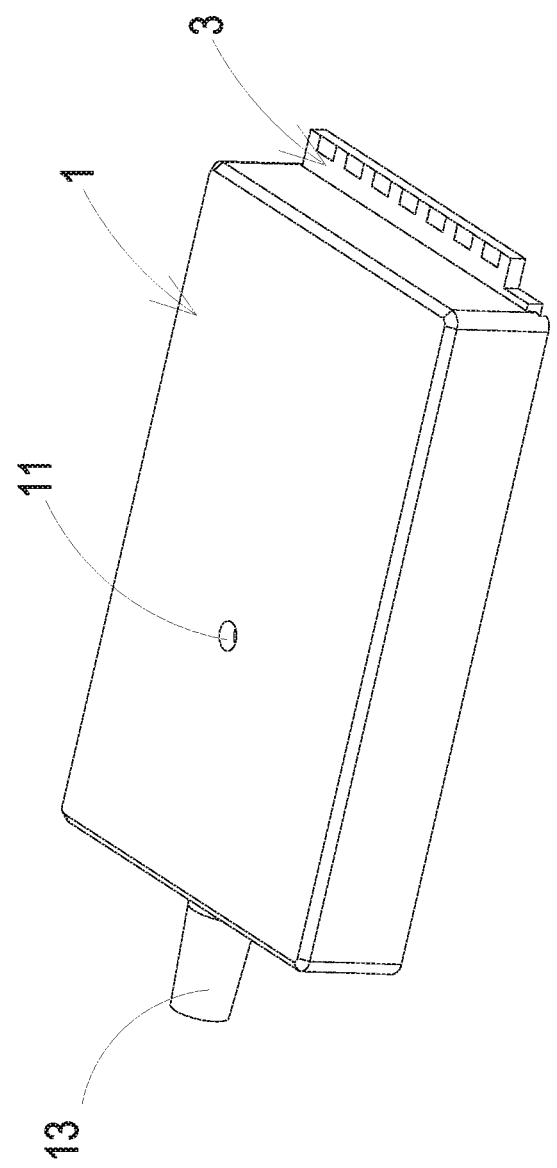
FIG. 1A illustrates a schematic perspective view of a blood pressure measurement module according to an exemplary embodiment of the present disclosure.
Figure 1B:
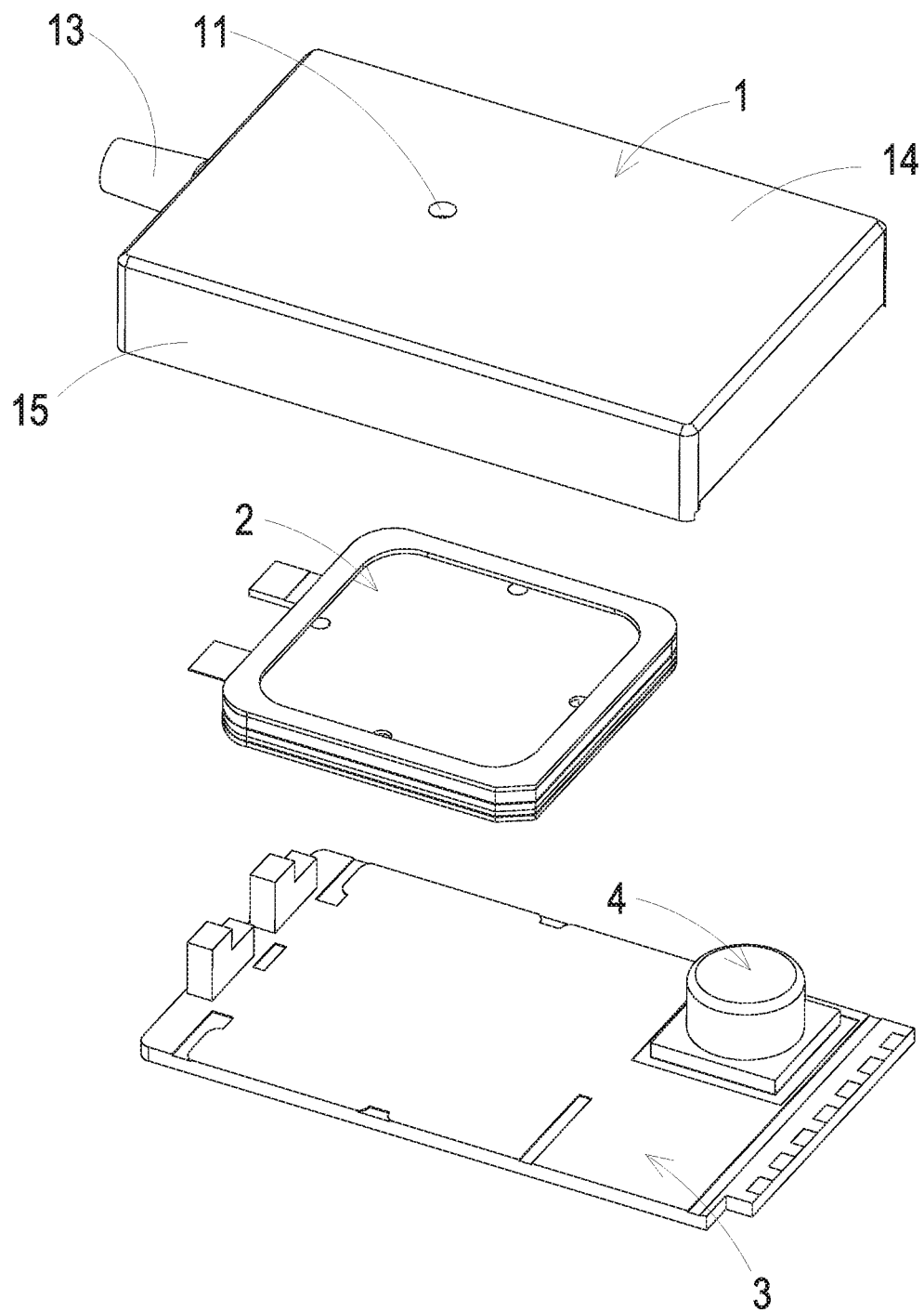
FIG. 1B illustrates a front exploded view of the blood pressure measurement module according to the exemplary embodiment of the present disclosure.
Figure 1C:
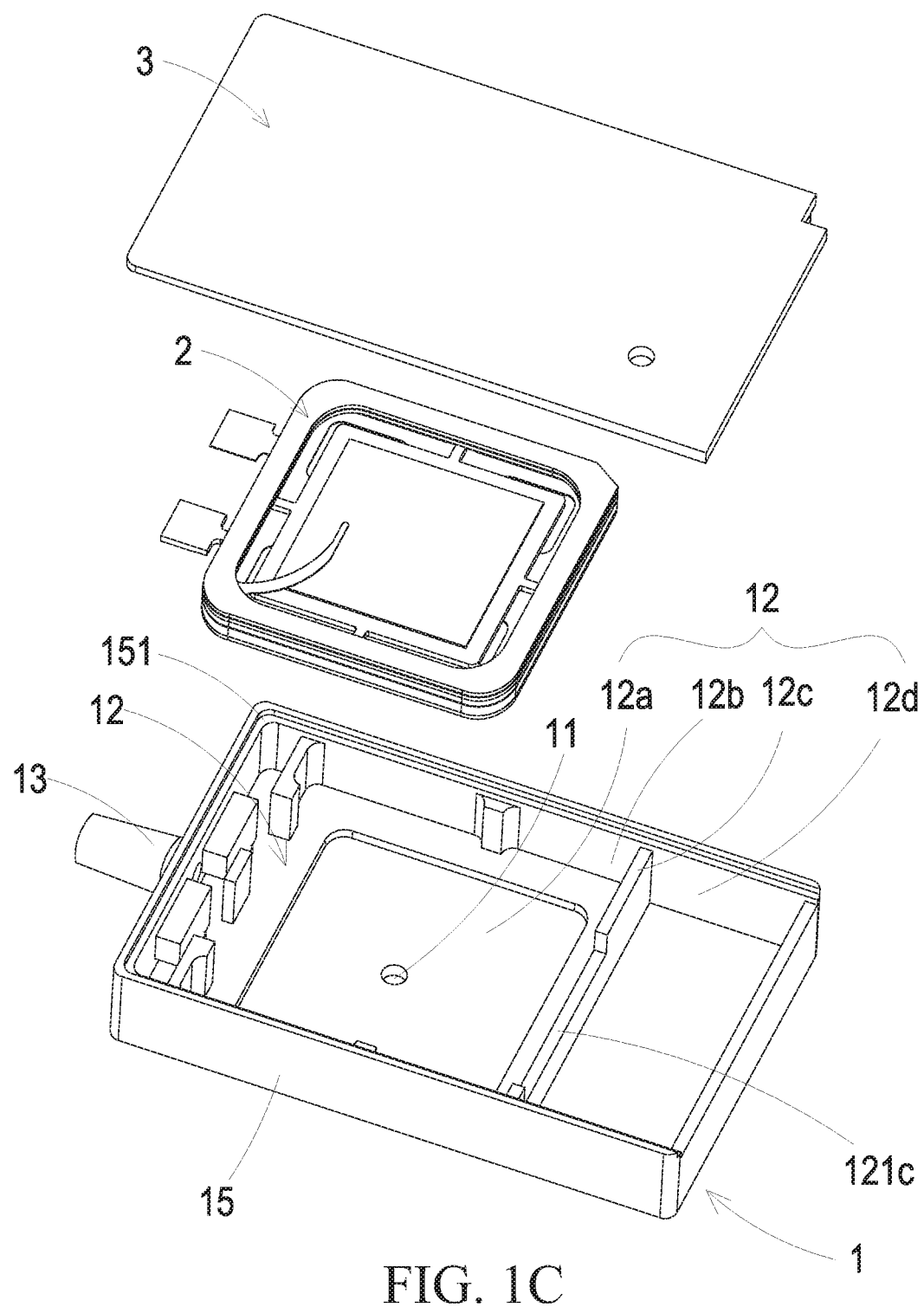
FIG. 1C illustrates a rear exploded view of the blood pressure measurement module according to the exemplary embodiment of the present disclosure.

Please refer to FIG. 1A to FIG. 1C. A blood pressure measurement module is provided and includes a top cover 1, a micro pump 2, a driving circuit board 3, and a pressure sensor 4.

The top cover 1 includes a gas inlet hole 11, an accommodation trough 12, an outlet channel 13, an upper plate 14, and a side wall portion 15. The side wall portion 15 perpendicularly extends from the periphery of the upper plate 14. The accommodation trough 12 is formed between the side wall portion 15 and the upper plate 14. The accommodation trough 12 includes a gas collection chamber 12a, a micro pump area 12b, a partition 12c, and a sensor area 12d. The accommodation trough 12 is separated by the partition 12c to form the micro pump area 12b and the sensor area 12d. The inner wall of the micro pump area 12b of the accommodation trough 12 is recessed to form the gas collection chamber 12a. The partition 12c has a notch 121c so that the micro pump area 12b is in communication with the sensor area 12d. The gas inlet hole 11 is located at the surface of the upper plate 14 and is in communication with the accommodation trough 12 and the gas collection chamber 12a thereof. The outlet channel 13 is disposed on the surface of the side wall portion 15 and is in communication with the accommodation trough 12. Moreover, the outlet channel 13 is connected to a gas bag 10 (as shown in FIG. 4), which is used for measuring a blood pressure.

Please refer to FIG. 1C. The micro pump 2 is accommodated in the micro pump area 12b of the accommodation trough 12, and the micro pump 2 covers the gas collection chamber 12a. Moreover, the side wall portion 15 has a groove 151, and the driving circuit board 3 is disposed in the groove 151 so as to cover the accommodation trough 12. The driving circuit board 3 is electrically connected to the micro pump 2 to provide a driving signal for the micro pump 2, thereby controlling the operation of the micro pump 2.

Figure 2:
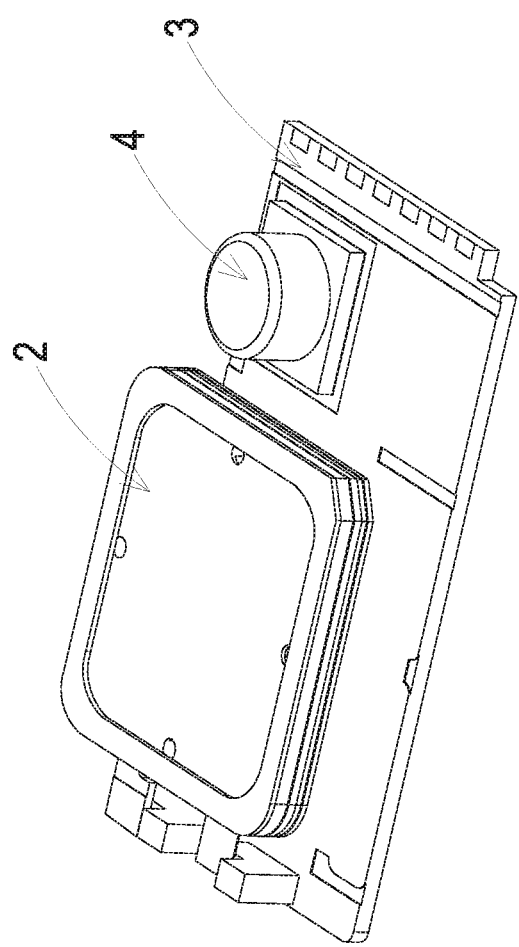
FIG. 2 illustrates a schematic perspective view showing that the pressure sensor disposed on the driving circuit board, according to the blood pressure measurement module of the exemplary embodiment.
Figure 3:
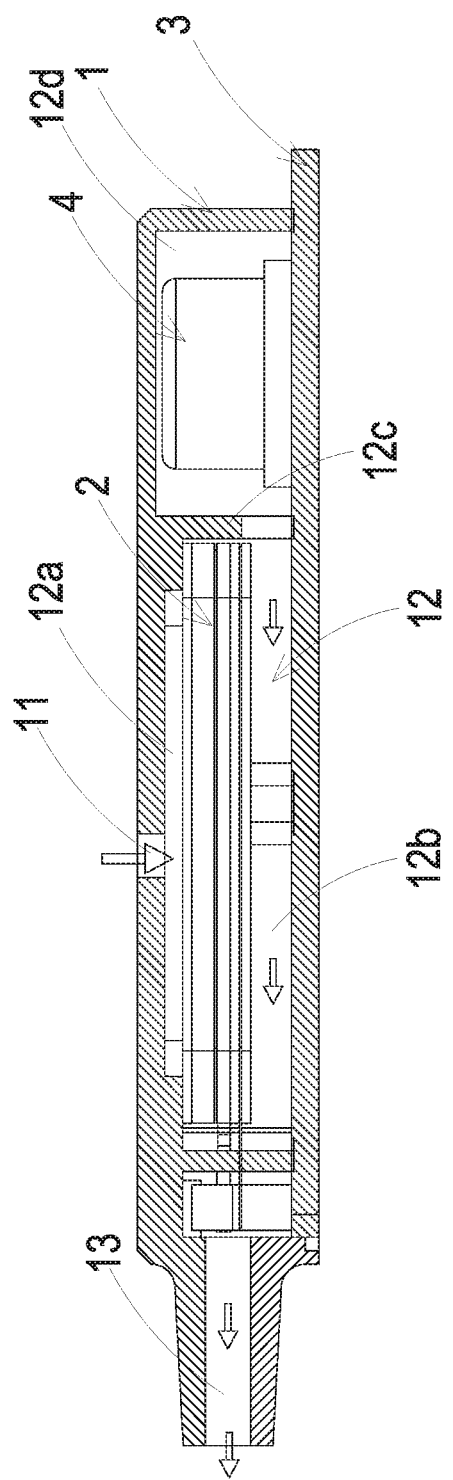
FIG. 3 illustrates a schematic cross-sectional view of the blood pressure measurement module of the exemplary embodiment.

Please refer to FIG. 2 and FIG. 3. The pressure sensor 4 is disposed on the driving circuit board 3 and electrically connected to the driving circuit board 3. When the driving circuit board 3 covers the accommodation trough 12, the pressure sensor 4 is accommodated in the sensor area 12d of the accommodation trough 12, so that the pressure sensor 4 may measure the pressure of the gas guided into the accommodation trough 12.

Figure 4:
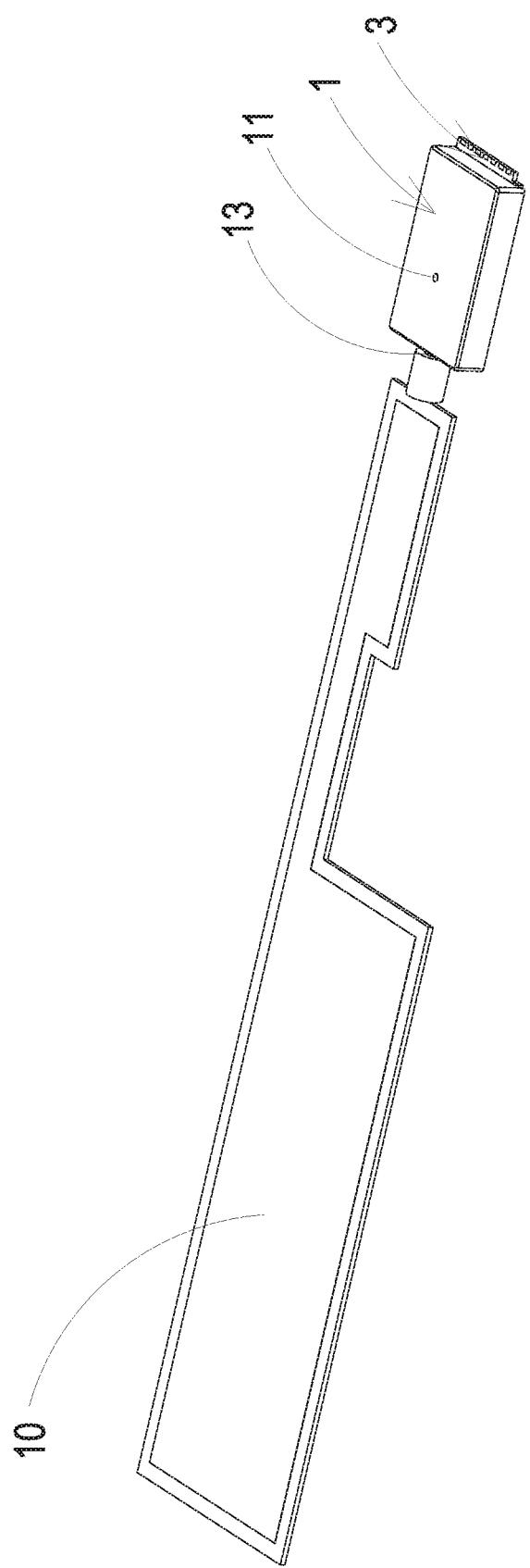
FIG. 4 illustrates a schematic view showing that the blood pressure measurement module of the exemplary embodiment is connected to a gas bag.

Please refer to FIG. 3 and FIG. 4. The driving circuit board 3 drives the micro pump 2 to operate so that the gas outside the top cover 1 is guided into the accommodation trough 12 through the gas inlet hole 11, and the gas is continuously guided to the outlet channel 13 and then is converged at the gas bag 10. Therefore, the gas bag 10 starts to inflate and then may be closely in contact with or press the skin of a user, and thus the blood pressure of the user can be measured through the pressure sensor 4. Moreover, when the pressure of the gas in the gas bag 10 measured by the pressure sensor 4 reaches a valve value, the driving circuit board 3 controls and stops the operation of the micro pump 2, thereby completing a pressure collection process of the gas bag 10.

Figure 5A:
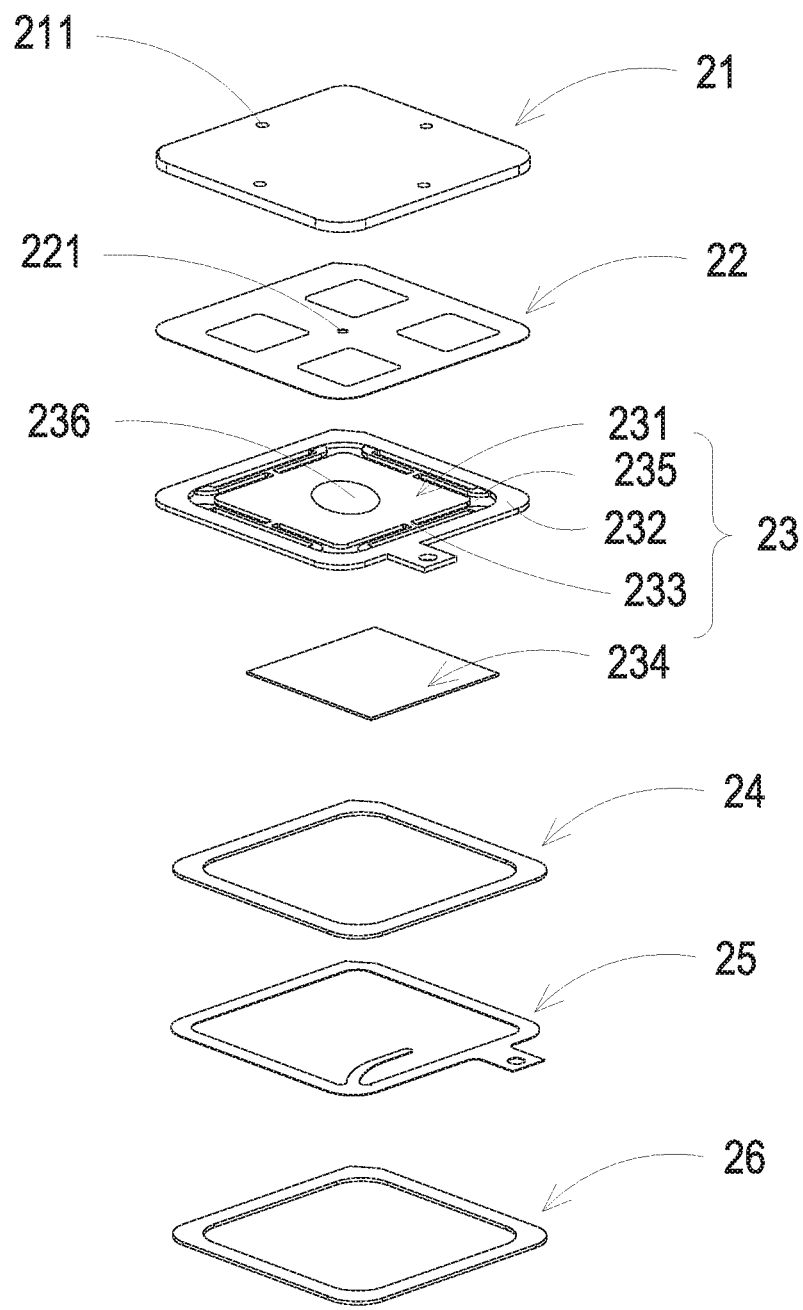
FIG. 5A illustrates a front exploded view of the micro pump in the blood pressure measurement module pf the exemplary embodiment.
Figure 5B:
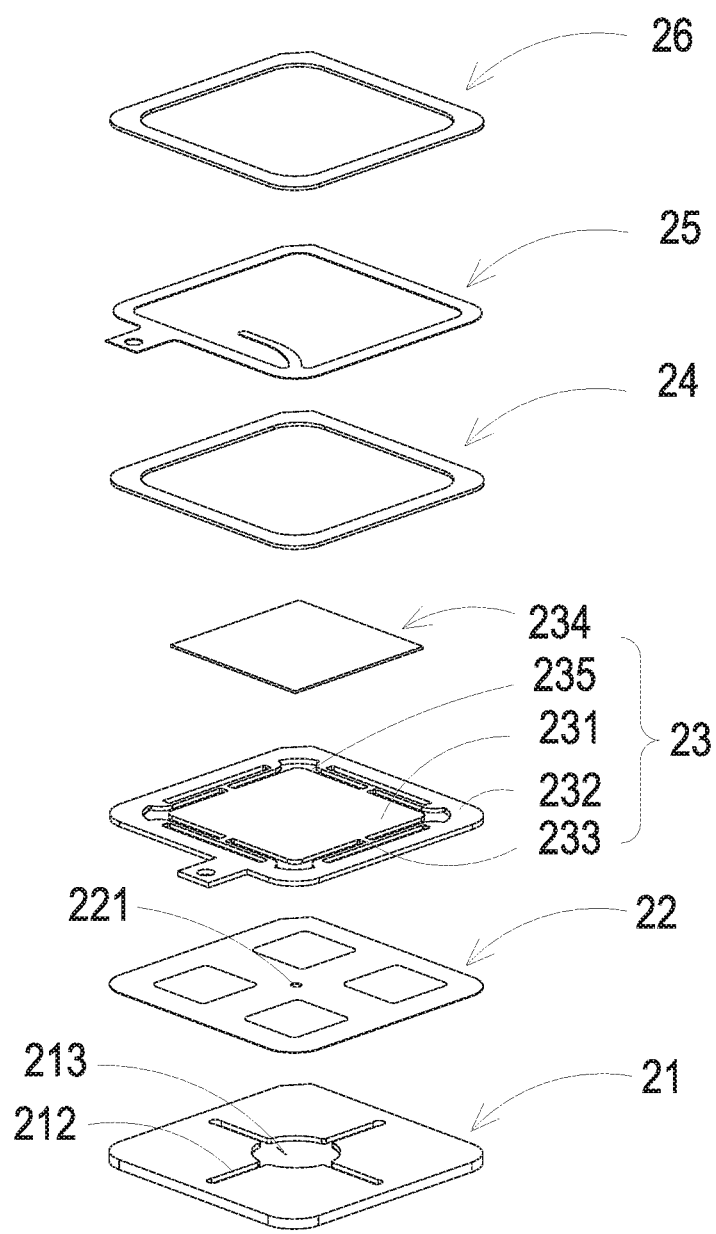
FIG. 5B illustrates a rear exploded view of the micro pump in the blood pressure measurement module of the exemplary embodiment.

Please refer to FIG. 5A and FIG. 5B. The micro pump 2 includes an inlet plate 21, a resonance sheet 22, a piezoelectric actuator 23, a first insulation sheet 24, a conductive sheet 25, and a second insulation sheet 26. The piezoelectric actuator 23 is disposed correspondingly to the resonance sheet 22. The inlet plate 21, the resonance sheet 22, the piezoelectric actuator 23, the first insulation sheet 24, the conductive sheet 25, and the second insulation sheet 26 are arranged sequentially and stacked with each other.

The inlet plate 21 has at least one inlet hole 211, at least one convergence channel 212, and a convergence chamber 213. In some embodiment, the number of the inlet hole 211 is preferably 2, but not limited thereto. The inlet hole 211 is defined through the inlet plate 21, so that the gas outside the micro pump 2 can flow into the micro pump 2 from the at least one inlet hole 211 due to the atmospheric pressure effect. The inlet plate 21 has the at least one convergence channel 212, and the number and the position of the convergence channel 212 are corresponding to the inlet hole 211 at the other side of the inlet plate 21. In this embodiment, the number of the inlet holes 211 is preferably 4, and the number of the convergence channels 212 corresponding to the inlet holes 211 is 4 as well. The convergence chamber 213 is disposed at the central portion of the inlet plate 21. One of two ends of each of the 4 convergence channels 212 is in communication with the corresponding inlet hole 211, and the other end of each of the 4 convergence channels 212 is in communication with the convergence chamber 213 at the central portion of the inlet plate 21. Thus, the gas entering into the convergence channels 212 from the inlet holes 211 is guided and is converged at the convergence chamber 213. In this embodiment, the inlet plate 21 is a one-piece element integrally formed with the inlet hole 211, the convergence channel 212, and the convergence chamber 213.

In some embodiments, the inlet plate 21 is made of stainless steel, but is not limited thereto. In some other embodiments, the depth of the convergence chamber 213 is substantially equal to the depth of the convergence channel 212, but is not limited thereto.

The resonance sheet 22 may be made of a flexible material, but is not limited thereto. Moreover, the resonance sheet 22 has a perforation 221 corresponding to the convergence chamber 213 of the inlet plate 21 and a periphery of the perforation 221 is a movable portion 222, whereby the gas in the convergence chamber 213 can pass through the resonance sheet 22. In some other embodiments, the resonance sheet 22 is made of copper, but is not limited thereto.

In some embodiment, the piezoelectric actuator 23 is assembled from suspension plate 231, an outer frame 232, at least one supporting element 233, and a piezoelectric element 234. The suspension plate 231 has a square shape, and the suspension plate 231 is capable of bending and vibrating. The outer frame 232 is disposed around the periphery of the suspension plate 231. The at least one supporting element 233 connected between the suspension plate 231 and the outer frame 232 to provide a flexible support for the suspension plate 231. The piezoelectric element 234 also has a square shape and is attached to one surface of the suspension plate 231 so as to drive the suspension plate 231 to bend and vibrate when the piezoelectric element 234 is applied with a voltage. The side length of the piezoelectric element 234 is smaller than or equal to a side length of the suspension plate 231. A plurality of gaps 235 is formed among the suspension plate 231, the outer frame 232, and the supporting element 233 for the gas passing therethrough. Moreover, the piezoelectric actuator 23 has a protruding portion 236 disposed on the other surface of the suspension plate 231. That is, the piezoelectric element 234 and the protruding portion 236 are respectively disposed on the two opposite surfaces of the suspension plate 231.

Figure 6A:
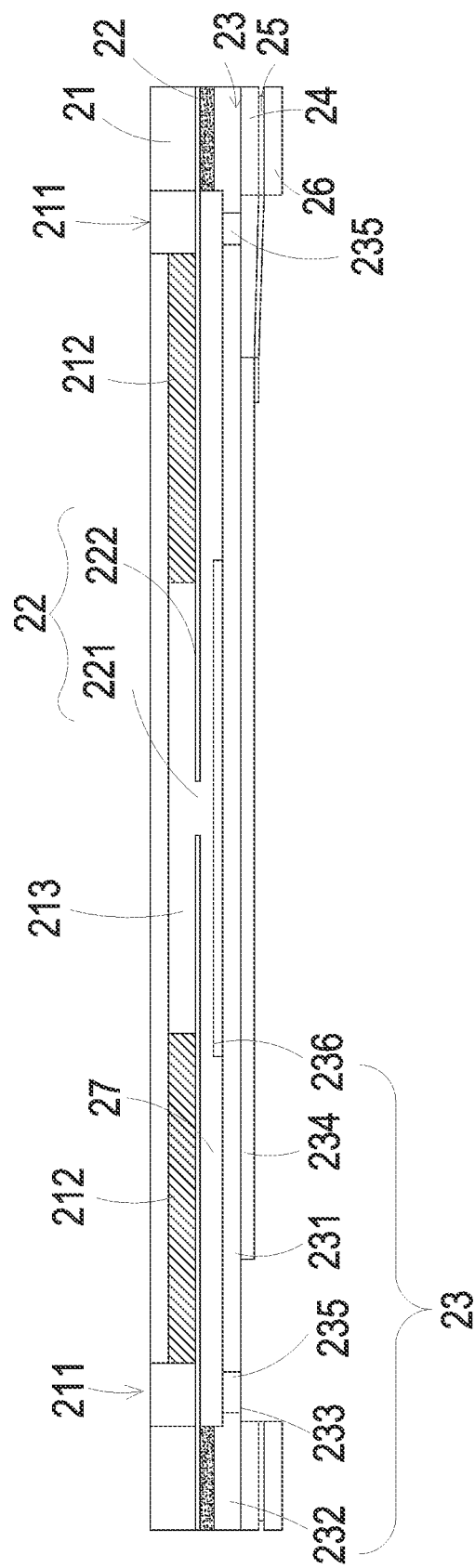
FIG. 6A illustrates a schematic cross-sectional view of the micro pump in the blood pressure measurement module of the exemplary embodiment.

As shown in FIG. 6A, in some embodiments, the inlet plate 21, the resonance sheet 22, the piezoelectric actuator 23, the first insulation sheet 24, the conductive sheet 25, and the second insulation sheet 26 are arranged sequentially and stacked with each other. The thickness of the suspension plate 231 of the piezoelectric actuator 23 is smaller than the thickness of the outer frame 232. Thus, when the resonance sheet 22 is stacked on the piezoelectric actuator 23, a chamber space 27 can be formed among the suspension plate 231, the outer frame 232, and the resonance sheet 22.

Figure 6B:
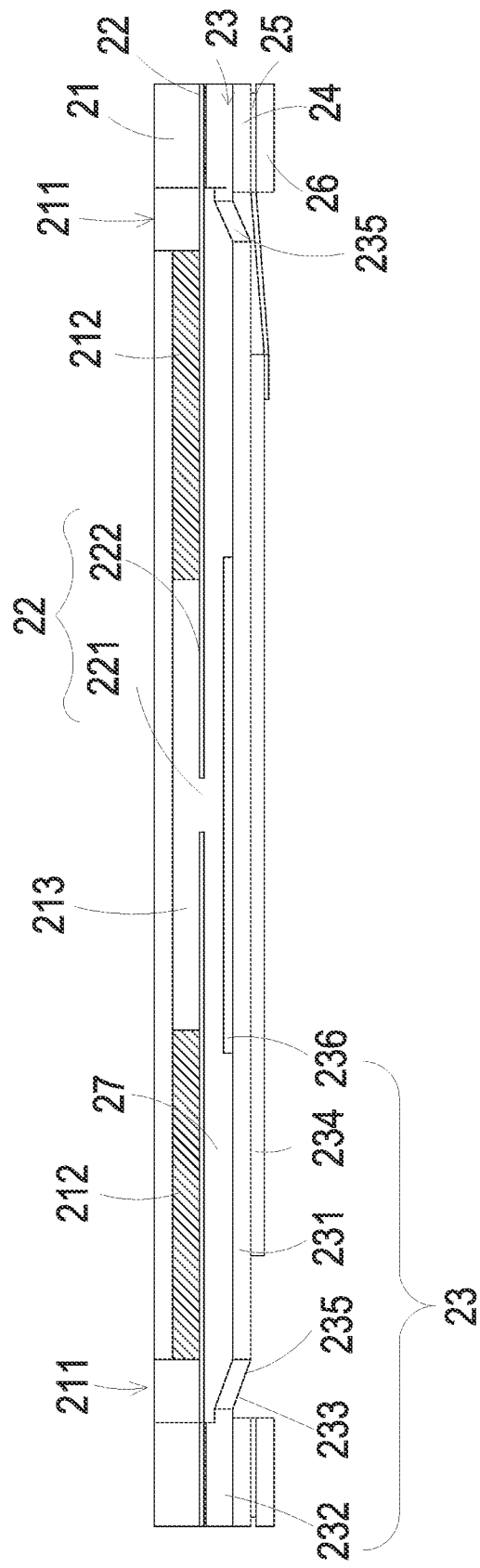
FIG. 6B illustrates a schematic cross-sectional view of the micro pump in the blood pressure measurement module according to another exemplary embodiment of the present disclosure.

Please refer to FIG. 6B. FIG. 6B shows another embodiment of the micro pump 2. Most of the elements in FIG. 6B are similar to the corresponding elements in FIG. 6A, which are not repeated here. The difference between the embodiment shown in FIG. 6B and the embodiment shown in FIG. 6A is that, when the micro pump 2 in FIG. 6B does not operate, the suspension plate 231 of the piezoelectric actuator 23 extends away from the resonance sheet 22 by a stamping process, so that the suspension plate 231 and the outer frame 232 are not aligned at the same level. The extended distance of the suspension plate 231 may be adjusted by the supporting elements 233. In such embodiments, the supporting elements 233 are not parallel to the suspension plate 231, so that part of the piezoelectric actuator 23 has a convex profile.

Figure 6C:
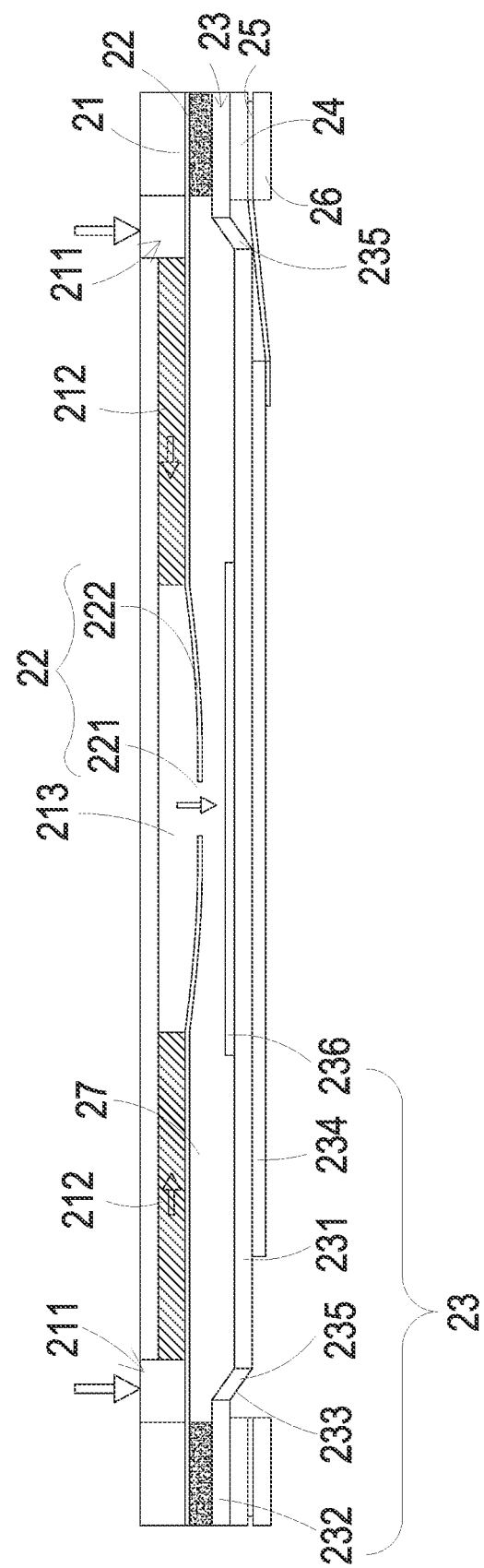
FIG. 6C to FIG. 6E illustrate schematic cross-sectional views showing the micro pump according to the exemplary embodiment of the present disclosure at different operation steps.
Figure 6D:
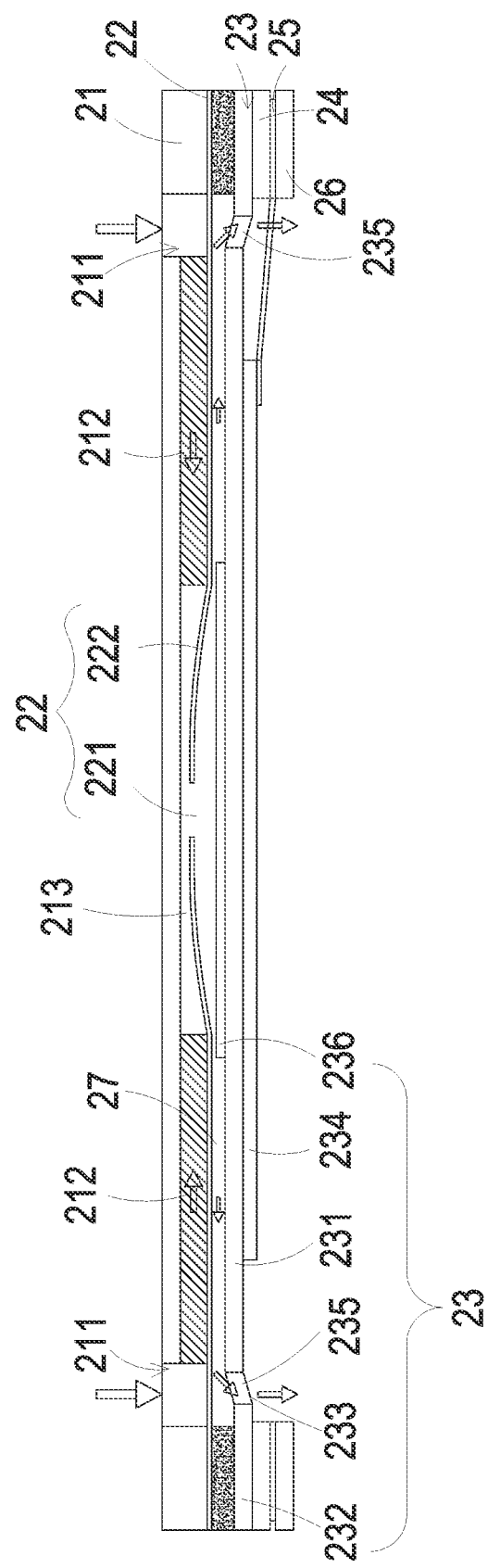
Figure 6E:
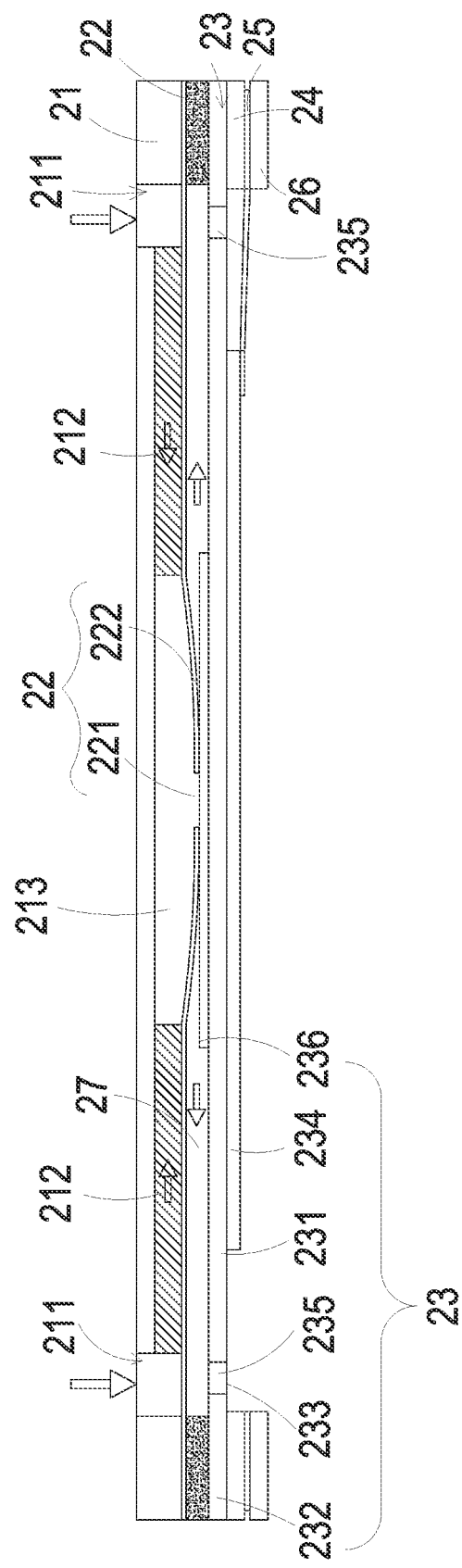

In order to understand the operation steps of the aforementioned micro pump 2 in transmitting gas, please refer to FIG. 6C to FIG. 6E. Please refer to FIG. 6C first, the piezoelectric element 234 of the piezoelectric actuator 23 deforms after being applied with a driving voltage, and the piezoelectric element 234 drives the suspension plate 231 to move away from the inlet plate 21. Thus, the volume of the chamber space 27 is increased and a negative pressure is generated inside the chamber space 27, thereby drawing the gas in the convergence chamber 213 into the chamber space 27. At the same time, owing to the resonance effect, the resonance sheet 22 is bent away from the inlet plate 21 correspondingly, which also increases the volume of the convergence chamber 213. Furthermore, since the gas inside the convergence chamber 213 is drawn into the chamber space 27, the convergence chamber 213 is in a negative pressure state as well. Therefore, the gas can be drawn into the convergence chamber 213 through the inlet hole 211 and the convergence channel 212. Then, please refer to FIG. 6D. The piezoelectric element 234 drives the suspension plate 231 to move toward the inlet plate 21, thereby compressing the chamber space 27. Similarly, since the resonance sheet 22 resonates with the suspension plate 231, the resonance sheet 22 also moves toward the inlet plate 21, thereby pushing the gas in the chamber space 27 to be transmitted out of the micro pump 2 through the at least one gap 235. Last, please refer to FIG. 6E. When the suspension plate 231 moves resiliently to its original position, the resonance sheet 22 still moves away from the inlet plate 21 due to its inertia momentum. At the time, the resonance sheet 22 compresses the chamber space 27, so that the gas in the chamber space 27 is moved toward the gap 235 and the volume of the convergence chamber 213 is increased. Accordingly, the gas can be drawn into the convergence chamber 213 continuously through the inlet holes 211 and the convergence channels 212 and can be converged at the convergence chamber 213. By continuously repeating the operation steps of the micro pump 2 shown in FIG. 6C to FIG. 6E, the micro pump 2 can make the gas continuously enter into the flow paths formed by the inlet plate 21 and the resonance sheet 22 from the inlet holes 211, thereby generating a pressure gradient. The gas is then transmitted outward through the gap 235. As a result, the gas can flow at a relatively high speed, thereby achieving the effect of gas transmission of the micro pump 2.

Figure 7A:
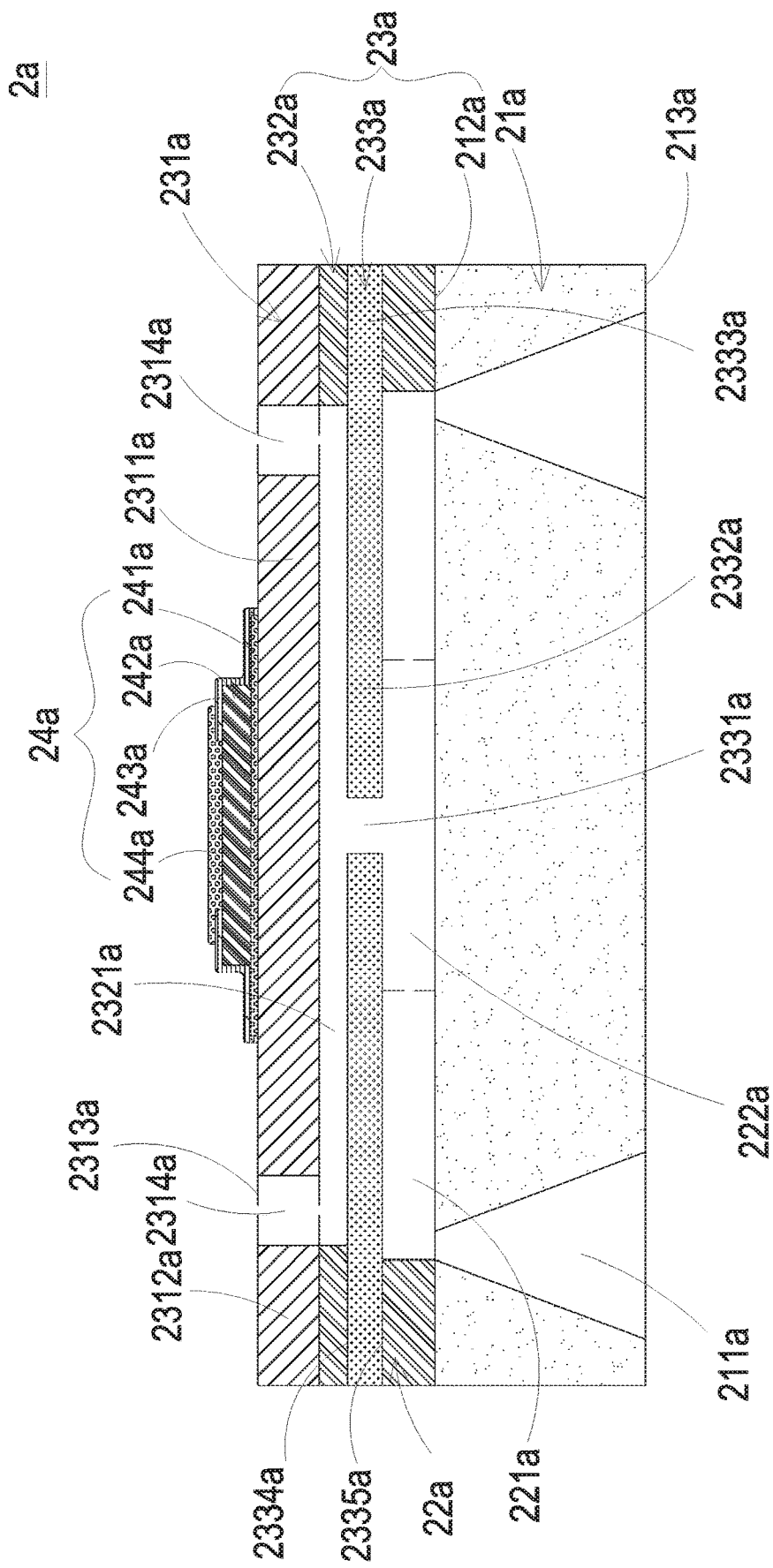
FIG. 7A illustrates a schematic cross-sectional view of a micro-electromechanical systems (MEMS) pump of the exemplary embodiment.
Figure 7B:
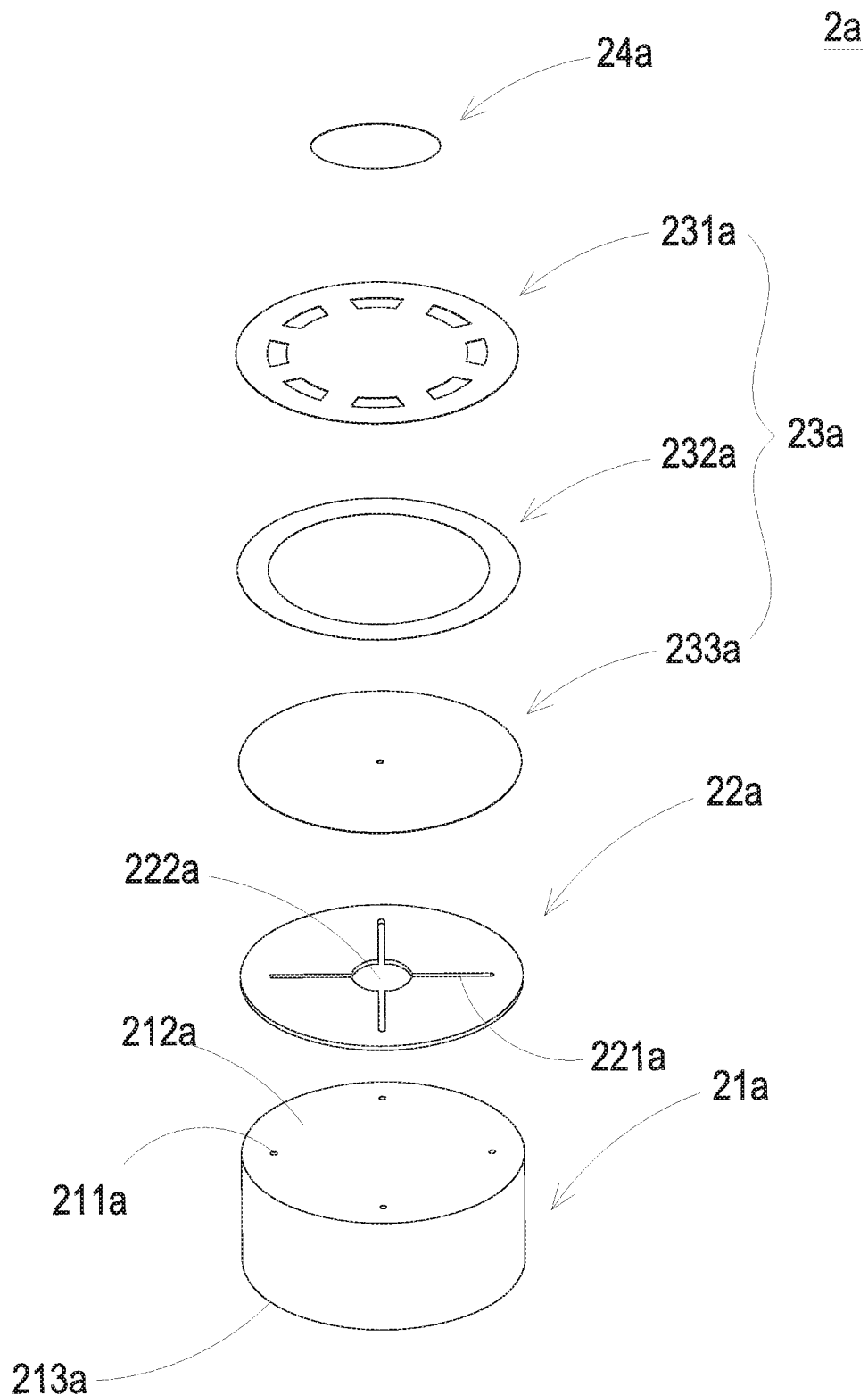
FIG. 7B illustrates a schematic exploded view of the MEMS pump of the exemplary embodiment.

In another embodiment, the micro pump 2 may be a microelectromechanical systems (MEMS) pump 2a. Please refer to FIG. 7A and FIG. 7B, the MEMS pump 2a includes a first substrate 21a, a first oxide layer 22a, a second substrate 23a, and a piezoelectric component 24a. It should be understood that in FIG. 7B, components of the MEMS pump 2a cannot be actually taken apart since the MEMS pump 2a is fabricated by semiconductor manufacturing processes including epitaxy, deposition, lithography, and etching. However, in order to clearly explain the detailed structure of the MEMS pump 2a, the exploded view is illustrated in FIG. 7B and used to explain the characteristics of the MEMS pump 2a.

The first substrate 21a is a silicon wafer (Si wafer), and the thickness of the Si wafer may be between 150 and 400 µm (micrometer). The first substrate 21a has a plurality of inlets 211a, a substrate first surface 212a, and a substrate second surface 213a. In this embodiment, the number of the inlets 211a is four, but not limited thereto. Each of the inlets 211a is defined through the first substrate 21a from the substrate second surface 213a to the substrate first surface 212a. In order to improve the inflow efficiency of the inlets 211a, each of the inlets 211a is a conical hole, that is, each of the inlets 211a is conical and tapered from the substrate second surface 213a to the substrate first surface 212a.

The first oxide layer 22a is a silicon dioxide ($SiO_2$) film. The thickness of the $SiO_2$ film is between 10 and 20 µm. The first oxide layer 22a is stacked on the substrate first surface 212a of the first substrate 21a. The first oxide layer 22a has a plurality of convergence troughs 221a and a convergence room 222a. The number and the position of the convergence trough 221a correspond to the number and the position of the inlets 211a in the first substrate 21a. In this embodiment, the number of the convergence troughs 221a is four as well. One of two ends of each of the four convergence troughs 221a is in communication with the corresponding inlet 211a in the first substrate 21a. The other end of the two ends of each of the four convergence troughs 221a is in communication with the convergence room 222a. Thus, after a gas enters into the first substrate 21a from the inlets 211a, the gas flows through the convergence troughs 221a and then is converged at the convergence room 222a.

The second oxide layer 232a is made of silicon oxide. The thickness of the second oxide layer 232a is between 0.5 and 2 µm. The second oxide layer 232a is formed on the silicon wafer layer 231a. The second oxide layer 232a is in a hollow ring shape, and the second oxide layer 232a and the silicon wafer layer 231a together define a vibration chamber 2321a. The silicon material layer 233a is in a circular shape and stacked on the second oxide layer 232a. The silicon material layer 233a is combined with the first oxide layer 22a. The silicon material layer 233a is a silicon dioxide ($SiO_2$) film, and the thickness of the silicon material layer 233a may be between 2 and 5 µm. The silicon material layer 233a has a through hole 2331a, a vibration portion 2332a, a fixed portion 2333a, a third surface 2334a, and a fourth surface 2335a. The through hole 2331a may be located at a center portion of the silicon material layer 233a. The vibration portion 2332a is located at a peripheral area of the through hole 2331a, and the vibration portion 2332a is perpendicularly corresponding to the vibration chamber 2321a. The fixed portion 2333a is located at a peripheral area of the silicon material layer 233a, and the vibration portion 2332a is fixed to the second oxide layer 232a by the fixed portion 2333a. The third surface 2334a is assembled with the second oxide layer 232a, and the fourth surface 2335a is assembled with the first oxide layer 22a. The piezoelectric component 24a is stacked on the actuation portion 2311a of the silicon wafer layer 231a. An outer peripheral portion 2312a is in a hollow ring shape and surrounds the periphery of the actuation portion 2311a. A plurality of connection portions 2313a are respectively connected between the actuation portion 2311a and the outer peripheral portion 2312a.

The piezoelectric component 24a includes a lower electrode layer 241a, a piezoelectric layer 242a, an insulation layer 243a, and an upper electrode layer 244a. The lower electrode layer 241a is stacked on the actuation portion 2311a of the silicon wafer layer 231a, and the piezoelectric layer 242a is stacked on the lower electrode layer 241a. The piezoelectric layer 242a and the lower electrode layer 241a are electrically connected through the contacted area between each other. Moreover, the width of the piezoelectric layer 242a may be smaller than the width of the lower electrode layer 241a, and thus the lower electrode layer 241a is not completely covered by the piezoelectric layer 242a. The insulation layer 243a is stacked on part of the piezoelectric layer 242a and the remaining portion of the surface of the lower electrode layer 241a which is not covered by the piezoelectric layer 242a. Then, the upper electrode layer 244a is stacked on the insulation layer 243a and the remaining portion of the surface of the piezoelectric layer 242a which is not covered by the insulation layer 243a, and thus the upper electrode layer 244a is electrically connected to the piezoelectric layer 242a through the contact between each other. Moreover, since the insulation layer 243a is inserted between the upper electrode layer 244a and the lower electrode layer 241a, a short circuit condition caused by the direct contact between the upper electrode layer 244a and the lower electrode layer 241a could be avoided.

Figure 8A:
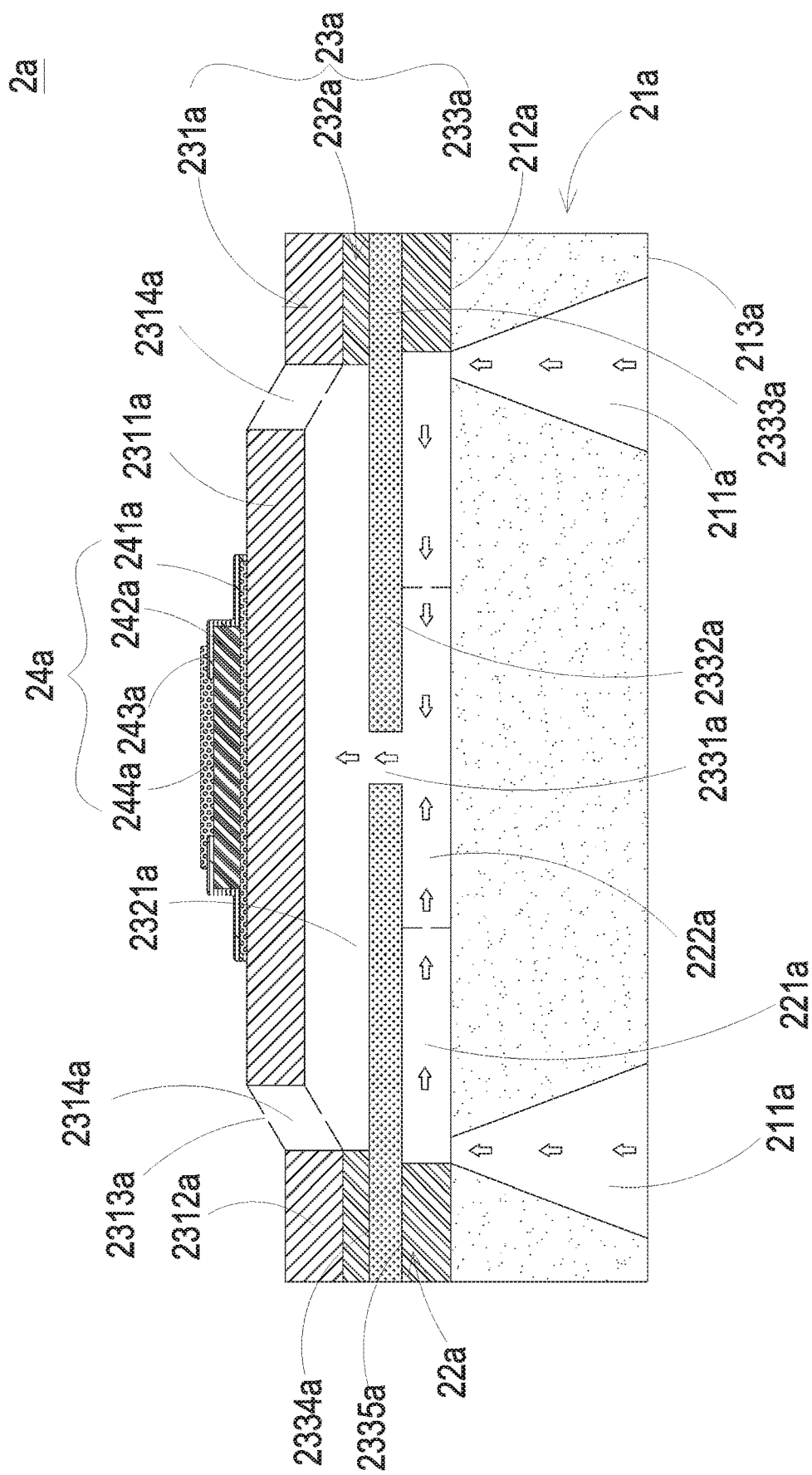
FIG. 8A to FIG. 8C illustrate schematic cross-sectional views showing the MEMS pump according to the exemplary embodiment of the present disclosure at different operation steps.
Figure 8B:
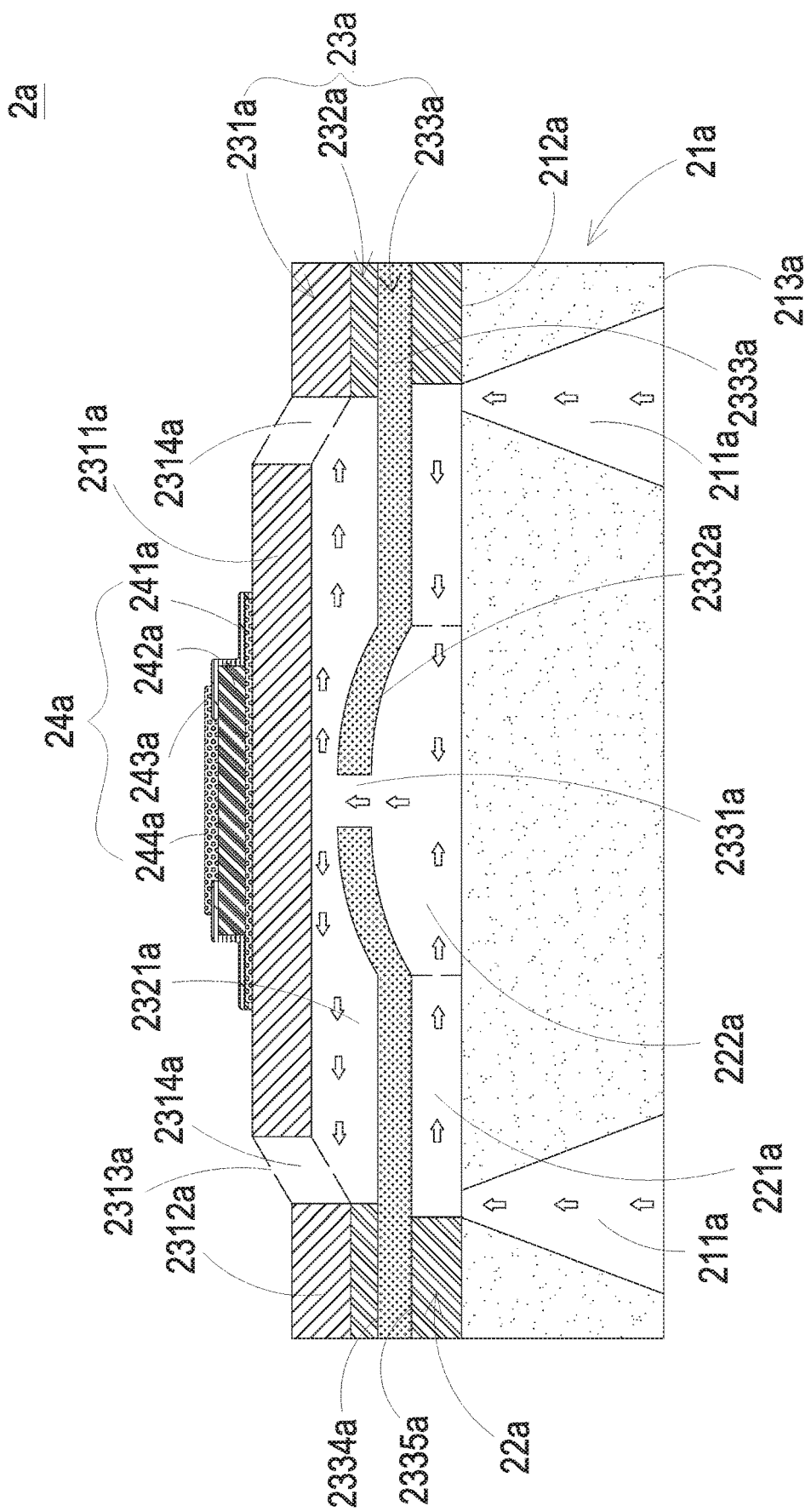
Figure 8C:
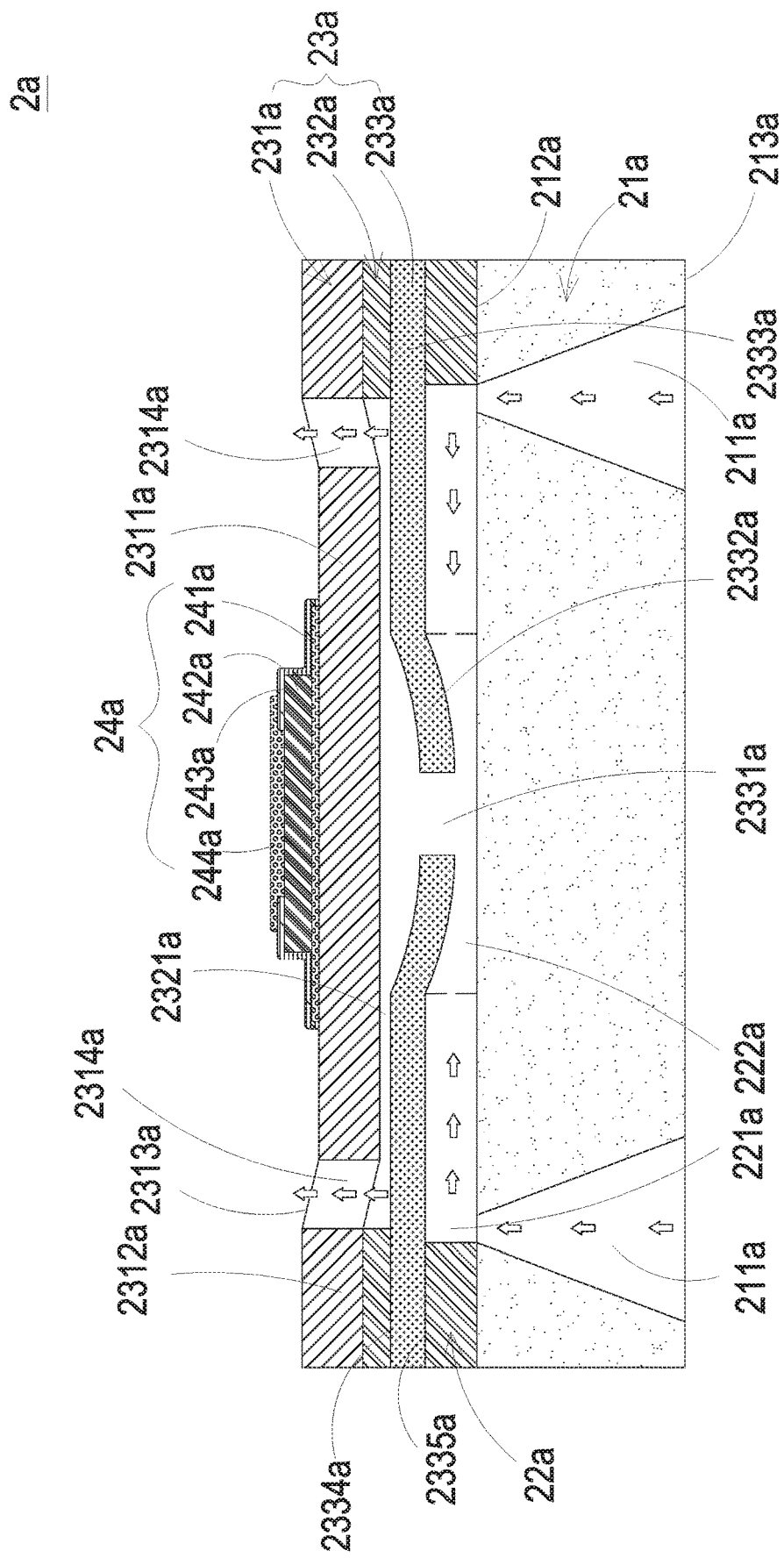

Please refer to FIG. 8A to FIG. 8C. FIG. 8A to FIG. 8C illustrate schematic cross-sectional views showing the micro-electromechanical systems (MEMS) pump 2a of the present disclosure at different operation steps. Please refer to FIG. 8A first, when the lower electrode layer 241a and the upper electrode layer 244a of the piezoelectric component 24a receive a driving voltage and a driving signal (not shown in the figure), the voltage and the signal are transmitted to the piezoelectric layer 242a. After the piezoelectric layer 242a is applied with the driving voltage and the driving signal, the piezoelectric layer 242a starts to deform because of the reverse piezoelectric effect, thereby driving the actuation portion 2311a of the silicon wafer layer 231a to move correspondingly. When the actuation portion 2311a is driven upwardly by the piezoelectric component 24a and thus the distance between the actuation portion 2311a and the second oxide layer 232a increases, the volume of the vibration chamber 2321a in the second oxide layer 232a increases as well. Hence, the pressure in the vibration chamber 2321a becomes negative, and thus the gas in the convergence room 222a of the first oxide layer 22a is drawn into the vibration chamber 2321a through the through hole 2331a. Please refer to FIG. 8B, when the actuation portion 2311a is driven upwardly by the piezoelectric component 24a, the vibration portion 2332a of the silicon material layer 233a is moved upwardly due to the resonance effect. When the vibration portion 2332a is moved upwardly, the space of the vibration chamber 2321a is compressed and the gas in the vibration chamber 2321a is pushed to fluid channels 2314a of the silicon wafer layer 231a, so that the gas can be discharged upwardly through the fluid channels 2314a. When the vibration portion 2332a is moved upwardly to compress the space of the vibration chamber 2321a, the volume of the convergence room 222a increases owing to the movement of the vibration portion 2332a. Hence, the pressure in the convergence room 222a becomes negative, and thus the gas outside of the MEMS pump 2a is drawn into the convergence room 222a through the inlets 211a. In the last step, as shown in FIG. 8C, when the actuation portion 2311a of the silicon wafer layer 231a is driven downwardly by the piezoelectric component 24a, the gas in the vibration chamber 2321a is pushed to the fluid channels 2314a and then discharged out. The vibration portion 2332a of the silicon material layer 233a is also driven by the actuation portion 2311a and thus moved downwardly; at the same time, the vibration portion 2332a compresses the gas in convergence room 222a and forces the gas to move to the vibration chamber 2321a through the through hole 2331a. Accordingly, when the actuation portion 2311a is driven upwardly by the piezoelectric component 24a again later, the volume of the vibration chamber 2321a greatly increases, thereby generating a larger suction force to draw the gas into the vibration chamber 2321a. By repeating the aforementioned steps, the actuation portion 2311a can be continually driven by the piezoelectric component 24a to move upwardly and downwardly, and the vibration portion 2332a is also driven to move upwardly and downwardly correspondingly. Thus, the internal pressure of the MEMS pump 2a can be changed periodically so as to draw and discharge the gas continually, thereby completing the pumping process of the MEMS pump 2a.

Please refer to FIGS. 1A to 1C again. In some embodiments, the length of the blood pressure measurement module of the present disclosure may be between 4 mm and 27 mm, the width of the blood pressure measurement module may be between 2 mm and 16 mm, and the height of the blood pressure measurement module may be between 1 mm and 8 mm. Therefore, the blood pressure measurement module is suitable for being combined with a portable electronic device. Moreover, in order to be suitable for being combined with a smart watch, the length of the blood pressure measurement module between 24 mm and 27 mm, the width of the blood pressure measurement module is between 14 mm and 16 mm, and the height of the blood pressure measurement module is between 6 mm and 8 mm.

Figure 9:
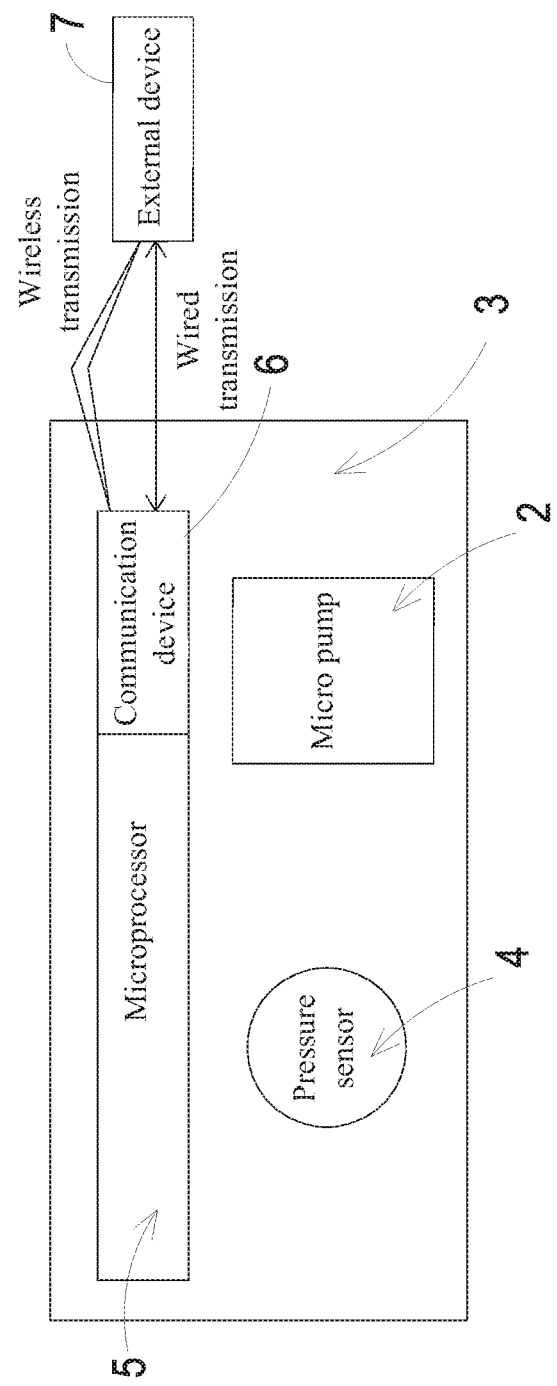
FIG. 9 illustrates a schematic block diagram showing that the blood pressure measurement module of the exemplary embodiment is connected to an external device.

Please refer to FIG. 9. The blood pressure measurement module may further include a microprocessor 5 and a communication device 6. The microprocessor 5 and the communication device 6 are disposed on the driving circuit board 3. The microprocessor 5 is configured to receive a measuring signal measured by the pressure sensor 4, to convert the measuring signal into an information data, and to transmit the information data through the communication device 6 to an external device 7 for storing, processing, or applying the information data. The information data can be transmitted to the external device 7 through a wired transmission, a wireless transmission, or both the wired transmission and the wireless transmission. In some embodiments, the external device 7 is at least one device selected from the group consisting of a cloud system, a portable device, and a computer system.

To sum up, in one or some embodiments of the present disclosure provides a blood pressure measurement module, the size of the pump may be reduced greatly, thereby achieving an effect of rapid inflation to the gas bag, whereby the blood pressure measurement module can be suitable for being disposed on a wearable device, such as a smart watch. Thus, the industrial value of the present application is very high, so the application is submitted in accordance with the law.

What is claimed is:

1. A blood pressure measurement module, comprising:
a top cover having a gas inlet hole, an accommodation trough, and an outlet channel, wherein the gas inlet hole and the outlet channel are respectively disposed on different surfaces of the top cover, and are respectively in communication with the accommodation trough, wherein an inner wall of the accommodation trough is recessed to form a gas collection chamber in communication with the gas inlet hole, wherein the outlet channel is connected to a gas bag, and wherein the top cover has a side wall portion, and the outlet channel is disposed on the side wall portion;
a micro pump disposed in the accommodation trough to cover the gas collection chamber;
a driving circuit board covering the accommodation trough, wherein the driving circuit board controls operation of the micro pump; and
a pressure sensor fixedly disposed on the driving circuit board and electrically connected to the driving circuit board, wherein the driving circuit board covers the accommodation trough of the top cover so as to detect a pressure of gas guided into the accommodation trough;
wherein the operation of the micro pump is controlled by the driving circuit board for a gas transmission, so that a gas outside the top cover is capable of being guided into the accommodation trough through the gas inlet hole, and the gas being continuously guided to the outlet channel and being converged at the gas bag by the micro pump, wherein the gas bag is configured to inflate and press against skin of a user, and the pressure sensor is configured to measure a blood pressure of the user, and wherein when the pressure of the gas in the gas bag measured by the pressure sensor reaches a valve value, the driving circuit board controls and stops the operation of the micro pump so as to complete a pressure collection process of the gas bag.

2. The blood pressure measurement module according to claim 1, further comprising a microprocessor and a communication device, wherein the microprocessor and the communication device are disposed on the driving circuit board, and the microprocessor is configured to receive a measuring signal measured by the pressure sensor, to convert the measuring signal into an information data, and to transmit the information data through the communication device to an external device for storing, processing or applying the information data.

3. The blood pressure measurement module according to claim 2, wherein the information data is transmitted to the external device through a wired transmission, a wireless transmission, or both the wired transmission and the wireless transmission.

4. The blood pressure measurement module according to claim 2, wherein the external device is at least one device selected from a group consisting of a cloud system, a portable device, and a computer system.

5. The blood pressure measurement module according to claim 1, wherein the micro pump comprises:
an inlet plate having at least one inlet hole, at least one convergence channel corresponding to the at least one inlet hole, and a convergence chamber, wherein the at least one inlet hole is configured to guide the gas outside the micro pump to flow into the micro pump, and the at least one convergence channel is configured to guide the gas from the at least one inlet hole to be converged at the convergence chamber;
a resonance sheet having a perforation corresponding to the convergence chamber, and a periphery of the perforation is a movable portion; and
a piezoelectric actuator disposed correspondingly to the resonance sheet;
wherein the inlet plate, the resonance sheet and the piezoelectric actuator are arranged sequentially and stacked with each other, wherein a chamber space is formed between the resonance sheet and the piezoelectric actuator, so that when the piezoelectric actuator is driven, the gas outside the micro pump is guided into the micro pump through the at least one inlet hole of the inlet plate, is converged at the convergence chamber via the at least one convergence channel, and flows through the perforation of the resonance sheet by a resonance effect between the piezoelectric actuator and the movable portion of the resonance sheet.

6. The blood pressure measurement module according to claim 5, wherein the piezoelectric actuator comprises:
a suspension plate having a square shape, wherein the suspension plate is capable of bending and vibrating;
an outer frame disposed around a periphery of the suspension plate;
at least one supporting element connected between the suspension plate and the outer frame to provide a flexible support for the suspension plate; and
a piezoelectric element having a side length, wherein the side length of the piezoelectric element is smaller than or equal to a side length of the suspension plate, and the piezoelectric element is attached to a surface of the suspension plate so as to drive the suspension plate to bend and vibrate when the piezoelectric element is applied with a voltage.

7. The blood pressure measurement module according to claim 5, wherein the micro pump comprises:
a suspension plate having a first surface and a second surface, wherein the first surface has a protruding portion;
an outer frame disposed around a periphery of the suspension plate and having an assembly surface;
at least one supporting element connected between the suspension plate and the outer frame to provide a flexible support for the suspension plate; and
a piezoelectric element attached to the second surface of the suspension plate so as to apply a voltage to the suspension plate to drive the suspension plate to bend and vibrate;
wherein the at least one supporting element is formed between the suspension plate and the outer frame, and the first surface of the suspension plate and the assembly surface of the outer frame are not coplanar, wherein a chamber gap is kept between the first surface of the suspension plate and the resonance sheet.

8. The blood pressure measurement module according to claim 5, wherein the micro pump further comprises a first insulation sheet, a conductive sheet, and a second insulation sheet, wherein the inlet plate, the resonance sheet, the piezoelectric actuator, the first insulation sheet, the conductive sheet, and the second insulation sheet are sequentially stacked and assembled with each other.

9. The blood pressure measurement module according to claim 8, wherein the micro pump is a microelectromechanical systems (MEMS) pump and comprises:
   a first substrate having a plurality of inlets, wherein each of the plurality of inlets is a conical hole;
   a first oxide layer stacked on the first substrate, wherein the first oxide layer has a plurality of convergence troughs and a convergence room, wherein the plurality of convergence troughs is in communication between the convergence room and the plurality of inlets;
   a second substrate combined with the first substrate, comprising:
      a silicon wafer layer, having:
         an actuation portion being in a circular shape;
         an outer peripheral portion being in a hollow ring shape and surrounding a periphery of the actuation portion;
         a plurality of connection portions respectively connected between the actuation portion and the outer peripheral portion; and
         a plurality of fluid channels surrounding the periphery of the actuation portion and located between the plurality of connection portions;
      a second oxide layer formed on the silicon wafer layer, wherein the second oxide layer is in a hollow ring shape, and the second oxide layer and the silicon wafer layer together define a vibration chamber; and
      a silicon material layer being in a circular shape and located at the second oxide layer, wherein the silicon material layer is combined with the first oxide layer, and the silicon material layer has:
         a through hole located at a center portion of the silicon material layer;
         a vibration portion located at a peripheral area of the through hole;
         a fixed portion located at a peripheral area of the silicon material layer; and
         a piezoelectric component being in a circular shape and stacked on the actuation portion of the silicon wafer layer.

10. The blood pressure measurement module according to claim 9, wherein the piezoelectric element comprises:
   a lower electrode layer;
   a piezoelectric layer stacked on the lower electrode layer;
   an insulation layer disposed on a part of a surface of the piezoelectric layer and a part of a surface of the lower electrode layer; and
   an upper electrode layer stacked on the insulation layer and a remaining portion of the surface of the piezoelectric layer where the insulation layer is not disposed, wherein the upper electrode layer is used for electrically connecting to the piezoelectric layer.

11. The blood pressure measurement module according to claim 1, wherein a length of the blood pressure measurement module is between 4 mm and 27 mm, a width of the blood pressure measurement module is between 2 mm and 16 mm, and a height of the blood pressure measurement module is between 1 mm and 8 mm.

12. The blood pressure measurement module according to claim 1, wherein a length of the blood pressure measurement module is between 24 mm and 27 mm, a width of the blood pressure measurement module is between 14 mm and 16 mm, and a height of the blood pressure measurement module is between 6 mm and 8 mm.

* * * * *